United States Patent [19]

Frazer

[11] Patent Number: Plant 6,871

[45] Date of Patent: Jun. 20, 1989

[54] DIEFFENBACHIA HYBRIDA HULA

[75] Inventor: Edwin J. Frazer, Brisbane, Australia

[73] Assignee: Hartman Plant Laboratories, Inc., Santa Paula, Calif.

[21] Appl. No.: 23,608

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Hale and Dorr

[57] ABSTRACT

A new and distinct cultivar of Dieffenbachia known as Dieffenbachia Hybrida Hula, which is a seedling cross between Marianne and Hoffmanii.

1 Drawing Sheet

The invention comprises a new and distinct cultivar of Dieffenbachia known as Dieffenbachia Hybrida Hula.

The new cultivar is a product of a seedling cross between Marianne and Hoffmanii.

The following observations, measurements and values describe plants grown in Alva, Fla. under greenhouse conditions that closely approximate those generally used in horticultural practice. All color references are measured against The Royal Horticultural Society Colour Chart. Colors are approximate as color depends on horticultural practices such as light level and fertilization rate among others.

The following traits have been repeatedly observed to be characteristics which in combination distinguish Dieffenbachia Hula from other commercially available Dieffenbachia.

DISTINCTIONS

1. Larger leaves than Camille.
2. Slightly fewer breaks than Camille.
3. Breaks that grow away from the main stem giving the plant a wide base.
4. The first break grows almost as tall as the main shoot.
5. Leaf pattern is the same as Camille.
6. The midrib is flexible enough to enable bending the leaf without damage.

The appearance and distinctive character of Hula is shown in the FIGURE which is a true color photograph of the cultivar in an eight-inch pot.

DESCRIPTION

Propagation: Asexual production either through tissue culture or division.

Plant: In a 6 inch pot, Hula will be approximately 18 cm to 22 cm from the soil surface to the junction of the petioles of the last two unrolled leaves and approximately 50 cm to 58 cm in width after approximately 26 weeks to 36 weeks under appropriate growing conditions from tissue culture. All measurements are based on the above parameters.

Stem:

*Growth pattern.*—The stem is erect in growth and will be approximately 1.8 cm to 2.2 cm in diameter 5 cm above the soil surface. Internode distance will be approximately 1.4 cm to 1.6 cm at a height of 3 cm above the soil.

*Color.*—The stem is faintly striped with green and light green.

Petiole (based on the third expanded leaf from apex of the main shoot):

*Pattern.*—The petiole has fleshy edges extending from the midrib that will be referred to as wings. The wings will be approximately 0.6 mm to 0.8 mm wide 1 cm below the leaf base. The wings extend from the base of the petiole to within approximately 0.7 cm to 0.9 cm of the leaf base. The apex of the wings is emarginate. The petiole follows the stem axis but diverges from the axis approximately 4.9 cm to 5.3 cm from the leaf base forming a horizontal distance from the edge of the stem to the leaf base of approximately 1.4 cm to 1.8 cm.

*Physical dimensions.*—The petiole will be approximately 8 cm to 12 cm from its base to the base of the leaf. The petiole will be approximately 5 mm to 7 mm in diameter one-half way between the top of the wing to the bottom of the leaf.

*Color and color pattern.*—The petiole wings will be green with faint white stripes and white dots. There will be a white area at the point where the wings end extending down on the petiole and the midrib will be green with faint white stripes and white dots.

Leaf:

*Growth pattern.*—The leaf will be ovate with a cuspidate/acuminate apex and a cordate base. The margin is entire. The leaf is asymmetric with the side of the leaf unrolling first having less surface area and less undulations on the leaf margin than the side unrolling last. The leaf is oriented 30° to the stem axis at the time of full unrolling changing to 80° to the stem axis as more leaves unroll above it. The midrib droops slightly over the length of the leaf. The leaf blade is flat and droops from the midrib to the margin.

*Physical dimensions.*—For the potsize and growing time indicated, the largest leaf will be approximately 25 cm to 29 cm long and approximately 11 cm to 13 cm wide. An average sized leaf will be approximately 15 cm to 17 cm long and approximately 6 cm to 8 cm wide. The leaf thickness is medium.

*Midrib.*—The midrib is thick and varies from a light green at the base to white at the tip.

*Primary veins.*—The primary veins are sunken into the adaxial side and protruding out of the abaxial side.

*Color and pattern.*—The adaxial surface of the mature, older leaf has a midrib color that is greener than 193A at the base of the leaf, changing to 157B on approach to the tip, and a leaf blade color of 155A, changing to 139A at approximately 5 mm. to approximately 15 mm. from the edge of the leaf. The abaxial surface of the mature, older leaf has a midrib color of 147D at the basal-surface, changing to 146 at the surface where the leaf blade is attached thereto; the leaf blade color is 155A, changing to 146A at approximately 12 mm. to approximately 20 mm. from the leaf edge, with blotches of 145A at the green-yellow interface. The adaxial surface of the newly-opened leaf has a midrib color of 155B, at the base of the leaf, changing to 155C on approach to the tip, and a leaf blade color of 150C, 154C, changing to 135A approximately 2 mm. to approximately 8 mm. from the leaf edge. The abaxial surface of the newly-opened leaf has a midrib color of 145C and a leaf blade color that is primarily 145D in the lower half of the leaf blade and 150 in the upper half, both halves changing to 137C approximately 2 mm. to approximately 6 mm. from the leaf edge.

*Texture.*—The leaf surface appears ribbed with the sunken minor veins giving a net-like texture. The surface appears dull.

Axillary breaks: There will be approximately 8 to 12 axillary breaks with at least 1 leaf expanded. Leaves will show color by the third leaf and will have true color and pattern by the fifth leaf.

Inflorescences: Not present.

Roots: Thick white roots with finer laterals.

General observations: Dieffenbachia Hula is a Camille type but varies in the following ways. Hula has larger leaves and fewer breaks. Hula has breaks that grow away from the main stem giving the base of the plant fullness. The first break develops into a major stem only slightly shorter than the main stem giving fullness to the top of the plant. The larger leaves give the plant more white and less green than Camille.

The midribs are flexible enough that the leaf can be bent double without damage.

I claim:

1. A new and distinct cultivar of Dieffenbachia as described and illustrated.

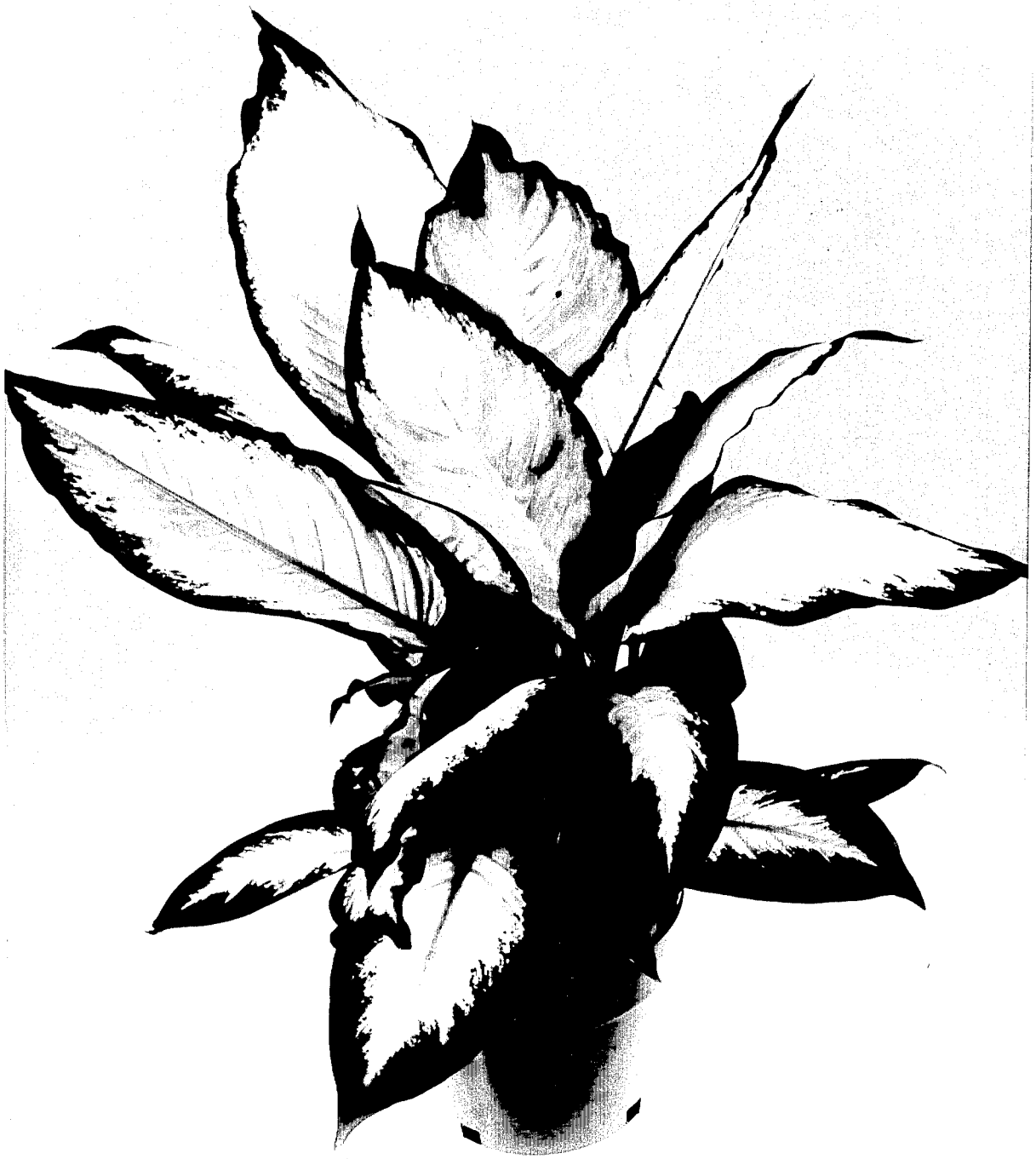

* * * * *